United States Patent [19]
Bissonette et al.

[11] Patent Number: 4,725,276
[45] Date of Patent: Feb. 16, 1988

[54] INTRAOCULAR LENS WITH CONTINUOUS POSTERIOR RING-LIKE MEMBER

[75] Inventors: Noel G. Bissonette, Richfield; Kenneth G. Uhler, Apple Valley, both of Minn.

[73] Assignee: Precision-Cosmet Co., Inc., Minnetonka, Minn.

[21] Appl. No.: 903,741

[22] Filed: Sep. 4, 1986

[51] Int. Cl.$^4$ ................................ A61F 2/16
[52] U.S. Cl. ........................................ 623/6
[58] Field of Search ............................ 623/6

[56] References Cited

U.S. PATENT DOCUMENTS

| Re. 31,626 | 7/1984 | Hoffer | 623/6 |
| 4,485,499 | 12/1984 | Castleman | 623/6 |
| 4,547,914 | 10/1985 | Castleman | 623/6 |
| 4,575,877 | 3/1986 | Herrick | 623/6 |

FOREIGN PATENT DOCUMENTS

85/04566 10/1985 PCT Int'l Appl. .................... 623/6

OTHER PUBLICATIONS

Precision-Cosmet Product Information Sheets.
Implantation Procedure for the Bechert 7mm One-Piece Posterior Chamber Lens; by Charles M. Bechert, M.D.
Implantation of the Kratz/Johnson 7.0mm Posterior Chamber Lens; by Richard P. Kratz, Stephen M. Johnson, M.D., 1983.
Implant Techniques, the Kamerling Capsular 90pcc; by William Kamerling.
Brochure, Large Optic Technology from Precision-Cosmet.

Primary Examiner—Ronald L. Frinks
Attorney, Agent, or Firm—Merchant, Gould, Smith, Edell, Welter & Schmidt

[57] ABSTRACT

An intraocular lens for use as an artificial lens impant in the posterior chamber of the human eye adjacent the posterior capsule, after extracapsular extraction is disclosed. The intraocular lens includes an optical lens body, and a continuous ring-like member spaced from the rear surface of the lens body by a plurality of supporting bosses which are attached to and extend directly rewardly from a peripheral portion of the rear surface of the lens body. The continuous ring-like member is preferably made of PROLENE ® and forms a resilient seal against the posterior capsule of the eye when implanted in the posterior capsule, thereby extending the period of time between cataract extraction and subsequent corrective micro-surgery necessitated by secondary cataract growth.

20 Claims, 8 Drawing Figures

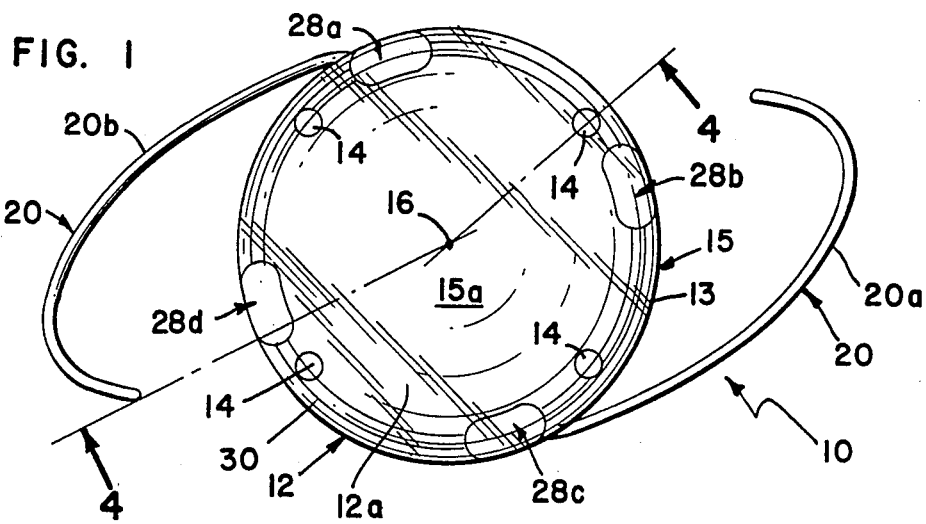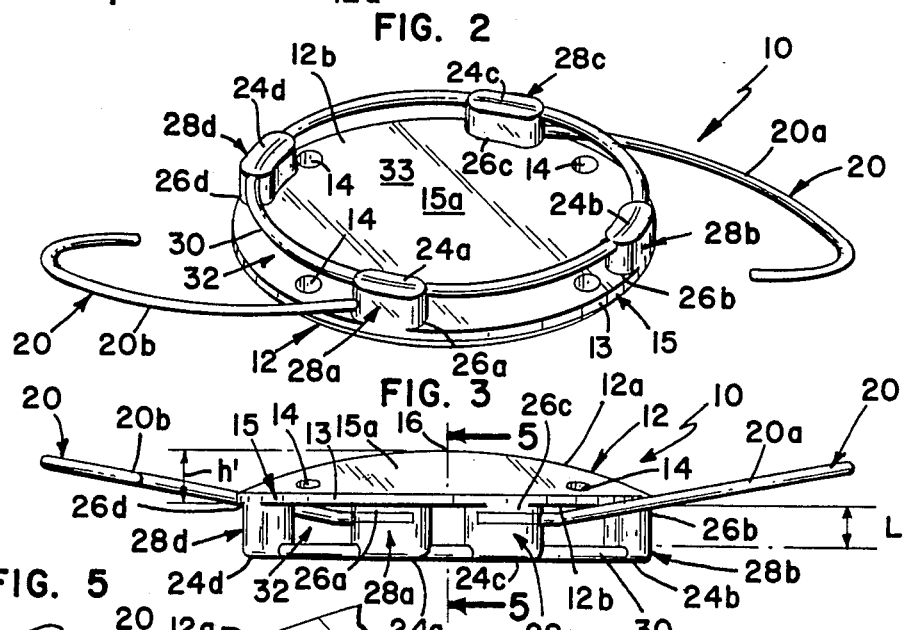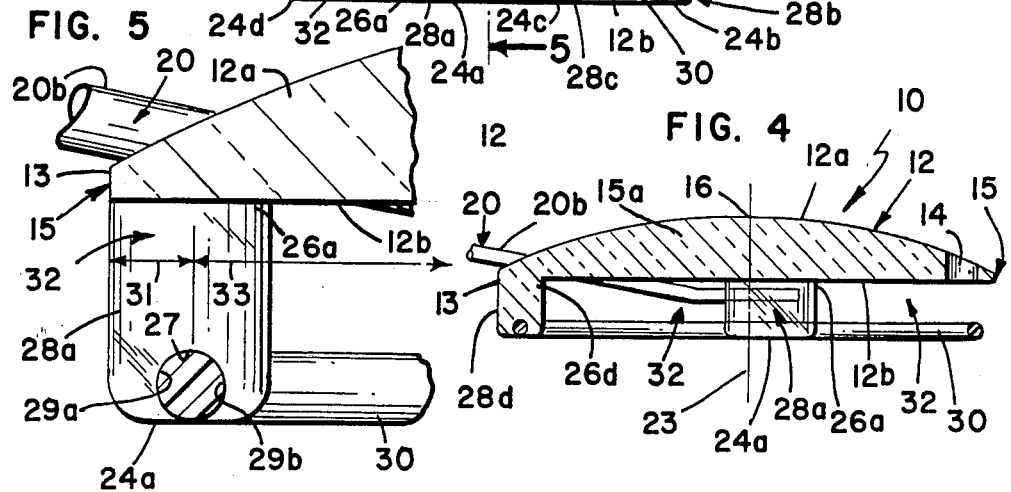

INTRAOCULAR LENS WITH CONTINUOUS POSTERIOR RING-LIKE MEMBER

TECHNICAL FIELD

This invention relates generally to intraocular lenses to be used as artificial lens implants in eyes from which the cataractous natural lens has been removed. More particularly, the present invention relates to an improved lens to be implanted in the posterior chamber of the eye after extracapsular extraction.

BACKGROUND

The implantation of an intraocular lens for restoring vision after cataract surgery is well-known in the art. In general, two forms of surgery are used to remove cataracts. These are extracapsular cataract extraction and intracapsular cataract extraction. (Discussed in U.S. Pat. No. Re. 31,626 to Hoffer).

Both intracapsular and extracapsular extraction eliminate light blockage due to the cataract. In intracapsular extraction the entire lens with the capsule and its content material intact is removed. In extracapsular cataract extraction the clouded cellular material within the lens capsule is extracted through an incision made through the anterior capsule of the lens without removing the transparent rear capsule wall (posterior capsule), suspensory ligaments (zonules) and peripheral portions of the anterior capsule (anterior capsule flaps).

Extracapsular extraction substantially reduces certain post-surgical complications which may result from intracapsular extraction. Particularly, one complication of intracapsular extraction is loss of vitreous humor from the eye through the incision made to accomplish the intracapsular extraction. Another undesirable complication of intracapsular extraction is Cystoid Macula Edema (CME). CME is an edema or swelling of the macula of the retina which may be caused by certain enzymes which are released from the iris and migrate through the vitreous humor back to the macula causing swelling. Vitreous loss and CME are both substantially reduced when extracapsular extraction is used since the posterior capsule remains in place, thereby preventing the vitreous humor from reaching the anterior chamber of the eye.

Following extraction of a cataractus lens, an intraocular lens is normally implanted in either the anterior or posterior chamber of the eye. A major problem associated with use of posterior chamber lenses is impairment of vision by secondary cataractic growth. While the lens capsule is inanimate, it is almost impossible to remove all living cells from it during cataract extraction. As a result, after sometime the cells grow and proliferate forming a bubbly glistening material known as Elschnig's pearls. Eventually the Elschnig's pearls impair vision necessitating subsequent corrective post operative surgery by invasive or non-invasive procedures.

Generally, known non-invasive post-operative corrective surgery such as laser surgery involves destroying the unwanted tissue behind the rear surface of the implanted lens by ionization. Laser surgery must be dimensionally precise to avoid ionizing or otherwise damaging the implanted lens and posterior capsule by radiation. Secondary cataratic growth can alternatively be removed by an invasive surgical procedure known as a discission in which a surgeon inserts a knife behind the lens and makes an opening in the intact posterior capsule. Both laser surgery and the discission procedure are more difficult when the lens implanted is a posterior chamber lens having a rear surface that seats directly against the posterior capsule. When this type of lens is implanted laser surgery can damage the lens. Particularly, the opening in the intact posterior capsule made during laser surgery results from a minor explosion at the point behind the lens where two laser beams intersect. If this explosion is too close to the lens it can cause small flaws or "nicks" in the lens. The lack of space between the rear surface of the lens and the posterior capsule also makes it difficult to perform a discission without displacing the lens.

Several available posterior chamber lenses include a structure which spaces the rear surface of the lens from the posterior capsule to facilitate corrective surgery. One such available posterior chamber lens is described in U.S. Pat. No. Re. 31,626 to Hoffer. The Hoffer lens includes an annular lip at the rear surface of the lens body which spaces the capsule from the edge of the rear surface of the lens. The Hoffer lens has several drawbacks. One disadvantage of the Hoffer lens is that collapse of the posterior capsule directly upon the central portion of the lens rear surface can occur. Another problem with the Hoffer lens is locating the open notch on the posterior of the lens during a discission. This can be difficult for the surgeon since the notch is frequently obscured from view by the iris.

U.S. Pat. No. 4,485,499 to Castleman, describes another type of posterior chamber lens including support structures for separating the lens body from the posterior capsule. One embodiment of the Castleman lens includes a solid annular portion and a central portion which is offset forwardly from the annular portion of the lens. The annular portion provides support for the posterior capsule when implanted but does not include an open space therein for insertion of a discission instrument or free flow of vitreous through the lens. Other supporting structures for the Castleman lens include spaced ridges fastened directly to the rear surface of the lens and spaced pegs connected by filaments. One specific arrangement of supporting pegs and connecting filaments described is a rectangular 4-peg combination with filaments on all four sides of the rectangle or on both sides and diagonals which defines a chamber roof profile for posterior capsule support. None of the embodiments of the Castleman lens include a continuous ring-like posterior resilient seal member which is spaced from and attached to the rear surface of the lens.

U.S. Pat. No. 4,575,877 to Herrick described yet another type of posterior chamber lens with a structure separating the lens body from the posterior capsule. The Herrick lens includes pliable loops each having an arcuate shaped mounting end with a protuberant member. The pliable loops define a posterior capsule framework. As in the case of the Hoffer and Castleman lenses, the Herrick lens does not include a continuous resilient ring-like seal against the posterior capsule.

It is believed that if the surgeon does a good job of cleaning the posterior capsule at the time of cataract extraction, a posterior chamber lens which provides a continuous resilient seal against the posterior capsule below the periphery of the lens when implanted will inhibit growth and migration of Elschnig's pearls into the central area of the posterior capsule, thereby significantly extending the period of time between cataract extraction and post-operative surgery. A continuous ring-like seal spaced from the rear surface of a posterior chamber type will also uniformly support the posterior capsule surface around the entire periphery of the lens to eliminate collapse of the capsule onto the rear surface of the lens. Inclusion of an open zone or free space through the lens at the rear surface of the lens body will facilitate both invasive and non-invasive post operative corrective surgery and provide for improved vitreous movement between the rear surface of the lens and the posterior capsule.

Accordingly, a substantial need exists for an improved posterior chamber lens which when implanted, provides a continuous resilient seal against the posterior capsule and an open zone or free space through the lens between the lens rear surface and the continuous resilient sealing member.

SUMMARY OF INVENTION

The present invention is an intraocular lens to be used as an artificial lens implant in the posterior chamber of the human eye adjacent the posterior capsule, after extracapsular extraction. The improved posterior chamber lens has a lens body with a peripheral portion and front and rear surfaces, a plurality of supporting bosses, and a continuous ring-like member connected to and spaced from the rear surface of the lens body by the supporting bosses.

The supporting bosses are attached at the inner ends thereof to the rear surface of the lens body and extend rearwardly from the peripheral portion of the rear surface of the lens body. Preferably, in order to provide adequate stability for the lens when implanted, a plurality of at least three supporting bosses extend directly rearwardly from the rear surface of the lens body. Each supporting boss terminates at a free end at which the continuous ring-like member is attached. While the continuous ring-like member can be affixed to the supporting bosses by any number of known means, in a preferred embodiment the continuous ring-like member is "swedged" (pressure fused or welded) into slots in the free ends of the supporting bosses.

In a preferred embodiment of the present invention the lens body and supporting bosses are made of a biologically tolerable and optically suitable medical grade plastic such as polymethylmethacrylate (PMMA). The continuous ring-like member can be made from a variety of materials that provide for a resilient seal, such as a nylon or an extrudable, biologically tolerable plastic. In a preferred embodiment, a posterior ring made from colored polypropylene (PROLENE ®), available from ETHICON, INC., U.S. Route 22 Somerville, N.J. is provided.

An important feature of the present invention is that the continuous ring-like member forms a resilient seal below the periphery of the lens body when the lens is implanted in the posterior chamber. Particularly, when implanted in the posterior chamber, the continuous ring-like member seats against and conforms to the posterior capsule along the entire circumference of the ring-like member. This continuous seal is believed to inhibit the growth and migration of Elschnig's pearls into the space between the rear surface of the optical portion of the lens body and the center area of the posterior capsule defined within the circumference of the continuous ring-like member. Accordingly, if at the time of initial cataract extraction a good job of cleaning the posterior capsule is done the period of time between cataract extraction and the need for post operative corrective surgery to remove secondary cataractic growth is extended. If post operative surgery is needed, the lens of the present invention provides an improved spacing structure to facilitate both invasive and non-invasive procedures. Particularly, the supporting bosses separate the lens body and continuous ring-like member to create a unique free space on open zone through the lens. This open zone also provides for improved vitreous movement between the rear surface of the lens and the posterior capsule. Another advantage of the present lens is that when implanted the continuous ring-like member together with the supporting bosses uniformly support the capsule surface around the entire peripheral portion of the lens thereby eliminating collapse of the posterior capsule onto the rear surface of the lens.

These and various other advantages and features of novelty which characterize the invention are pointed out with particularity in the claims annexed hereto and forming a part hereof. However, for better understanding the invention, its advantages and objects attained by its use, reference should be had to the drawings which form a further part hereof and the accompanying descriptive matter in which there is illustrated and described a preferred embodiment of the invention.

BRIEF DESCRIPTION OF THE DRAWINGS

FIG. 1 is a top plan view of a preferred embodiment of the intraocular lens of the present invention;

FIG. 2 is perspective view of the lens shown in FIG. 1;

FIG. 3 is a side elevational view of the lens shown in FIG. 1;

FIG. 4 is a sectional view taken along the line 4—4 in FIG. 1;

FIG. 5 is an enlarged sectional view taken along the line 5—5 in FIG. 3;

DETAILED DESCRIPTION OF THE INVENTION

Figure 6:
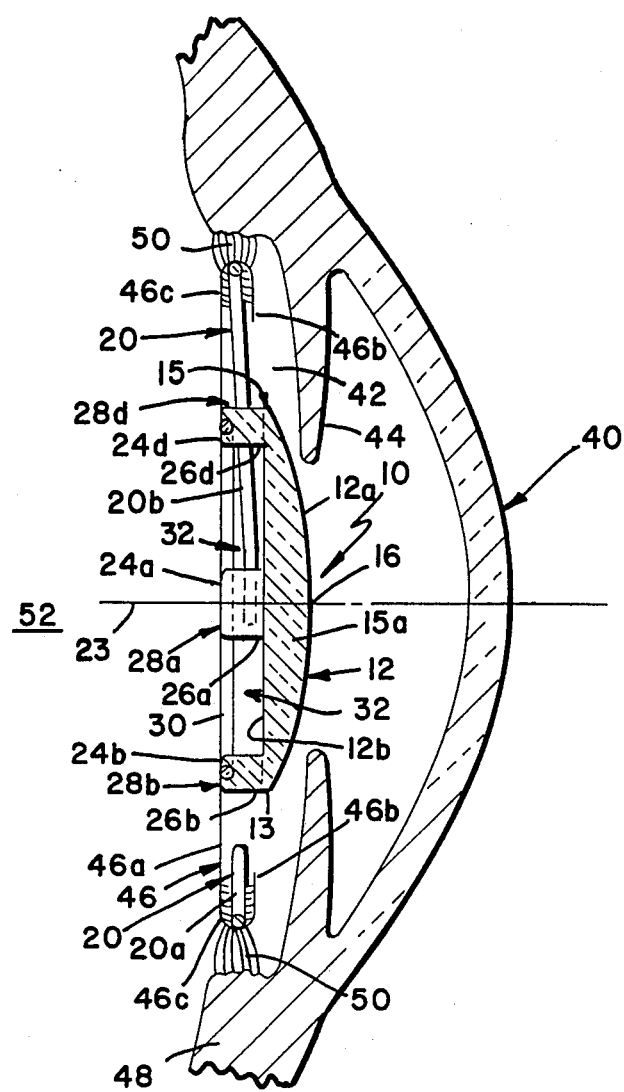
FIG. 6 is a simplified cross-sectional schematic view of an eyeball with the lens of the present invention implanted in the posterior chamber.

Referring to the drawings, wherein like numerals represent like parts throughout the several views, an intraocular lens designated generally as 10 incorporating the present invention is shown in FIGS. 1-6.

The intraocular lens 10 includes an optical lens body 12. Preferrably, although not necessarily, the lens body 12 is of a plano-convex cross-section as seen best in FIGS. 3 and 4. Referring to FIGS. 1-4, the lens body 12 has an anteriorly convex front surface 12a, including an apex 16 and a substantially planar rear surface 12b. A peripheral zone or portion 15 including the outer periphery or circumference 13 surrounds the optical zone 15a of the lens body. The height h' of the lens body 12, as best seen in FIG. 3, can be characterized as the distance from the apex 16 to the bottom surface 12b measured along the optical axis 23 of lens body 12. The lens body 12 is made from a medical grade, biologically tolerable and optical suitable material such as polymethylmethacrylate (PMMA). As seen in FIGS. 1 and 2 the lens body 12 can be provided with positioning holes 14.

A feature of the lens 10 of the present invention is the inclusion of a plurality of supporting bosses 28a, 28b, 28c, 28d attached at the inner ends 26a, 26b, 26c, 26d thereof to the peripheral portion 15 of the rear surface 12b and extending rearwardly therefrom. The supporting bosses 28a, 28b, 28c, 28d can be made from a number of biological tolerable plastic materials such as PMMA or polypropylene. PMMA supporting bosses are preferred. It will be appreciated that a lens 10 having a PMMA lens body 12 and PMMA supporting bosses 28a, 28b, 28c, 28d can be formed as an integral one-piece structure by forging or machining. Alternatively, the lens body 12 and supporting bosses 28a, 28b, 28c, 28d may be formed separately by a number of known methods such as injection molding and lathing. The supporting bosses 28a, 28b, 28c, 28d can be secured to the rear surface 12b by various means such as adhesives, chemical fusion and press fitting the inner ends 26a, 26b, 26c, 26d into fixed receiving holes in the lens body 12. In the preferred embodiment the lens body and supporting bosses are compression molded.

Referring to FIG. 2, in the embodiment shown, four supporting bosses 28a, 28b, 28c, 28d are spaced generally equal distant from each other along the peripheral portion 15 of the rear surface 12b. The supporting bosses 28a, 28b, 28c, 28d extend directly rearwardly away from the rear surface 12b and terminate at free ends 24a, 24b, 24c, 24d. As best seen in FIG. 5, in the preferred embodiment the free ends 24a, 24b, 24c, 24d each include a slot 27 defined generally by opposite walls 29a, 29b.

Figure 7:
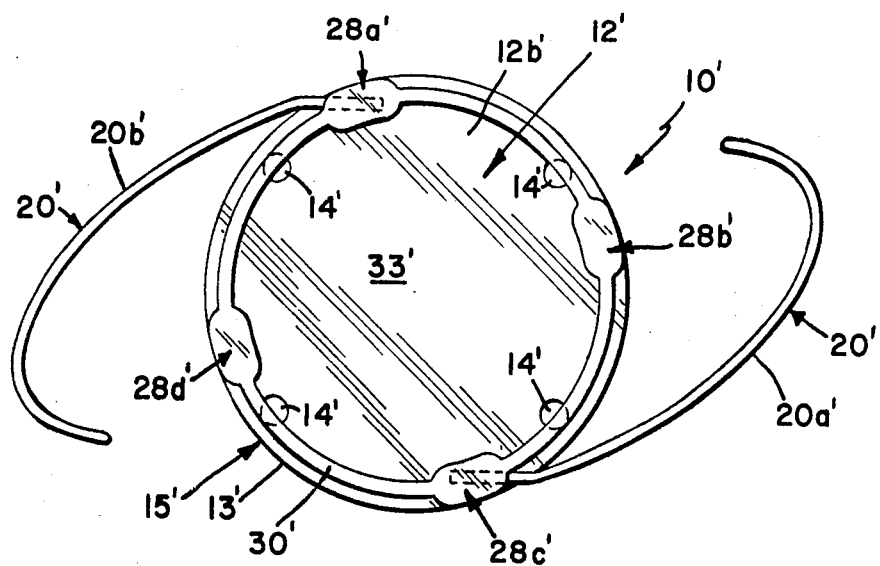
FIG. 7 is a bottom plan view of an alternate embodiment of the intraocular lens of the present invention.
Figure 8:
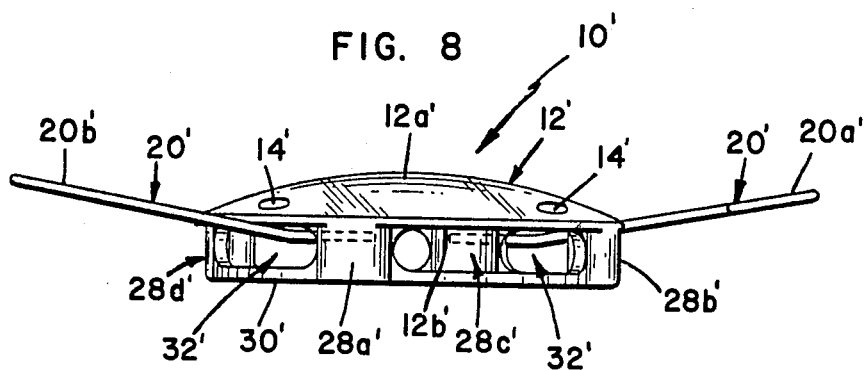
FIG. 8 is a side elevational view of the alternate embodiment of the intraocular lens shown in FIG. 7.

Referring to FIGS. 1-3 the lens 10 of the present invention includes a continuous ring-like member 30, which forms a resilient seal against the posterior capsule 46a (FIG. 6) when the lens 10 is implanted in the eye. The continuous ring-like member 30 is made integral with the lens body 12 at the free ends 24a, 24b, 24c, 24d of the supporting bosses 28a, 28b, 28c, 28d. The continuous ring-like member can be secured to the free ends 24a, 24b, 24c, 24d by a number of known methods. As best seen in FIG. 5, in a prefered embodiment, the continuous ring-like member 30 is secured to each free end 24a, 24b, 24c, 24d between the walls 29a, 29b of each slot 27. More particularly, the continuous ring-like member 30 is secured in slots 27 by a process known as "swedging" in which the continuous ring-like member 30 is secured into the slots 27 with either a heated or cold tool which crimps or pinches the adjacent walls 29a, 29b about the continuous ring-like member 30. The cold "swedging" procedure is preferred when making lens 10 according to the present invention. It will be appreciated that "swedging" the continuous ring-like member 30 at the free ends 24a, 24b, 24c, 24d eliminates the need for adhesives. In an alternate embodiment 10' of the present invention shown in FIGS. 7-8 (similar parts are referenced with prime (') notations) the lens body 12', supporting bosses 28a', 28b', 28c', 28d', and continuous ring like member 30' are formed as an integral one-piece structure by known methods such as molding.

Referring to FIGS. 2 and 3, the rear surface 12b and the continuous ring-like member 30 are coaxially spaced apart in parallel alignment by the supporting bosses 28a, 28b, 28c, 28d. The rear surface 12b, supporting bosses 28a, 28b, 28c, 28d and continuous ring-like member 30 define a free space or open zone 32 along and adjacent to the rear surface 12b of the lens body 12. As best seen in FIG. 3 the continuous ring-like member is spaced from the rear surface 12b of the lens body a distance L which defines one dimension (height) of the free space 32 which corresponds to the distance between the rear surface 12b and the continuous ring-like member 30 at the free ends 24a, 24b, 24c, 24d of the supporting bosses 28a, 28b, 28c, 28d. The free space 32 also includes a center zone 33 within the circumferance of the continuous ring-like member 30 and a segmented outer zone 31 best seen in FIG. 5 which extends from the circumferance of the continuous ring-like member 30 outward to the periphery 13 of the rear surface 12b of the lens body 12 between each set of adjacent supporting bosses 28a, 28b, 28c, 28d.

It is to be understood that the segmented outer zone 31 of the free space 32 allows for insertion of a discission instrument between the rear surface 12b and the continuous ring-like member 30 into the central zone 33 of the free space 32 between the rear surface 12b of the optical zone 15a of the lens body 12 and the posterior capsule 46a (FIG. 6). This minimizes the potential for dislodging the lens 10 when the discission cut is made. The continuous ring-like member 30 and supporting bosses 28a, 28b, 28c, 28d also sufficiently space the lens body 12 from the posterior capsule 46a to allow focusing of a laser in the central zone 33 so that ionization of the posterior capsule 46a and lens body 12 are minimized during laser surgery. The free space 32 of the present lens 10 further provides for improved vitreous movement in the posterior chamber 42 of the eye 40. Particularly, when the lens 10 is implanted, the free space 32 between the rear surface 12b of the lens body 12 and the continuous ring-like member 30 allow vitreous humor to flow freely into and out of the free space 32 between the rear surface 12b of the lens body 12 and the posterior capsule 46a to improve the supply of nutrients to the area of the lens 10.

The continuous ring-like member 30 can be made from a wide range of biologically tolerable materials which will conform to the surface of the posterior capsule 46a (FIG. 6) and form an effective resilient seal. These materials include nylon and a number of biologically tolerable extrudable plastic materials, such as PMMA, and transparent and colored polypropylene (PROLENE ®). Preferably, the lens 10 of the present invention includes a continuous PROLENE ® ring having a thickness or cross-sectional diameter which is considerably less than the thickness of the peripheral portion 15 of the lens body 12. Particularly, the cross-sectional diameter of the preferred PROLENE ® ring is between about 0.15 mm and 0.25 mm. It is believed the continuous ring-like member 30 serves as a barrier which inhibits growth and migration of Elschnig's pearls into the area of the posterior capsule 46a within the circumference of the continuous ring-like member 30 where accumulation of the Elschnig's pearls can impair vision.

As seen in FIGS. 1 and 2 the preferred embodiment of the lens 10 includes four supporting bosses 28a, 28b, 28c, 28d. However, it is to be appreciated that any number of three or more supporting bosses spaced about the peripheral zone 15 of the rear surface of 12b of the lens body 12 will be sufficient to support the continuous ring-like member 30 in a manner maintaining a resilient seal against the posterior capsule 46a when the lens 10 is implanted.

The dimensions of the lens 10 and spacing of the lens body 12 and continuous ring-like member 30 can be varied consistent with the purposes of the present invention. However, preferably, the height L of the free space 32 from the rear surface 12b of the lens to the continuous ring-like member for optimum spacing of the rear surface 12b from the posterior capsule 46a (FIG. 6) is from about 0.7 mm to 0.9 mm. Further, the typical lens body having a plano-convex upper surface will have a diameter from about 6.0 mm to 7.0 mm with a clear optical zone diameter from about 5.3 mm to 6.3 mm. The peripheral zone 15 distance from the edge of the optical zone 15a to the outer periphery 13 is about 0.60 mm to 0.70 mm. The continuous ring-like member 30 will be parallel with the rear surface 12b of the lens body 12 and inset from the outer periphery 13 about 0.15 mm to 0.25 mm.

The posterior chamber lens 10, as previously mentioned, is used after extracapsular cataract extraction. As seen in FIG. 6, the lens 10 is implanted in a human eye 40 in the posterior chamber 42 behind the iris 44. Preferably, the cataract has been extracted from the capsule bag 46 leaving intact the posterior capsule 46a and an annular flap portion 46b forming a cleft or fornix 46c. The capsular bag 46 is connected to the ciliary muscle in the eye wall 48 via suspensory ligaments 50. Vitreous humor in the region 52 behind the capsular bag 46 is prevented from flowing forward by the posterior capsule 46a which assumes a generally planar shape.

For purposes of positioning and holding the lens 10 in the posterior chamber 42 (FIG. 6), the lens 10 is provided with resilient loops or haptic members 20 interconnected to and extending outwardly from the lens body 12 at or adjacent the peripheral portion thereof 15. Referring to FIGS. 1-4 in the preferred embodiment shown, two curved elongated haptic members 20a,b are affixed to and extend outwardly from generally oppositely positioned supporting bosses 28a, 28c along an arc exterior to the periphery 13 to fix the lens 10 in operative alignment with the optical axis of the eye 40 (FIG. 6). The arc traversed by the haptic members 20a, 20b is substantially circular and curved toward the periphery 13 of the lens body 12. While in the embodiment shown the haptic members 20a, 20b extend from the supporting bosses 28a, 28c, the haptic members can extend outwardly from points anywhere within the peripheral zone 15 of the lens body 12. It is to be appreciated that arcuate shaped haptics of a wide variety of shapes and designs are known such as "J" shaped (U.S. Pat. No. 4,468,820 to Uhler et al; U.S. Pat. No. 4,435,855 to Pannu) and "C" shaped (U.S. Pat. No. 4,477,931 to Kelman; U.S. Pat. No. 4,494,254 to Lopez). The lens 10 of the present invention could incorporate haptics with any of these known shapes and designs, including a single haptic member or a combination of a single flexible haptic member together with an inflexible haptic support element. The haptic members 20a, 20b are made from a flexible, compressible, resilient plastic material such as PMMA or polypropylene. Preferably, like the lens 10, the haptics 20a, 20b are made from PMMA.

Referring to FIG. 6, when the posterior chamber lens 10 is implanted in the posterior chamber of the 42 of the eye 40, the haptic elements 20a, 20b, support the lens 10 by engaging the cleft or fornix portion 46c,; thereby fixating the position of the lens 10 in the eye 40. When the lens 10 is implanted in the posterior chamber 42 the continuous ring-like member 30 resiliently seals against the posterior capsule 46a with the rear surface 12b of the lens body spaced forward of and separated from the posterior capsule 46a by continuous ring-like member 30, the supporting bosses 28a, 28b, 28c, 28d and intervening free space 32.

While the above embodiments have been described in reference to plano-convex lens it is be understood that the lens of the present invention is also applicable to bi-convex lenses. The bi-convex lens would have a convex upper surface and a convex bottom surface. The present invention could also be used utilized with plano-concave lenses. Other modifications of the invention will be apparent to those skilled in the art in light of the foregoing description.

This description is intended to provide specific examples of individual embodiments which clearly disclose the present invention. Accordingly, the invention is not limited to the embodiment shown or to the use of elements having specific configurations in shape as presented herein. All alternative modifications and variations of the present invention which follow in the spirit and broad scope of the appended claims are included.

What is claimed is:

1. An intracular lens for implantation in the posterior chamber of a human eye adjacent the posterior capsule, after extracapsular extraction; said intraocular lens comprising:
   (a) a lens body having a peripheral portion and front and rear surfaces;
   (b) means for holding said lens body in said posterior chamber;
   (c) a plurality of supporting bosses attached to and extending rearwardly from said periphery portion of said rear surface of said lens body, said bosses each having a free end;
   (d) a continuous ring-like member; and
   (e) means for attaching said continuous ring-like member to said free ends of said support supporting bosses, said ring-like like member forming a resilient seal with the posterior capsule of the eye when said lens body is implanted in the posterior capsule, said continuous ring-like member engaging and uniformly supporting the posterior capsule around the entire peripheral poriton of said lens body; said continuous ring being swedged to the free ends of said supporting bosses.

2. An intraocular lens according to claim 1 wherein said lens body is substantially plano-convex, said supporting bosses extending directly rearwardly from a planar rear surface of said lens body.

3. An intraocular lens according to claim 1 wherein said lens holding means comprises a plurality of lens centering haptic members attached to said supporting bosses, said haptic members extending peripherally outwardly from said lens body.

4. An intraocular lens according to claim 1 wherein said supporting bosses provide an open zone at the rear surface of said lens body to permit the insertion of a discission instrument therethrough.

5. An intraocular lens according to claim 1 wherein said continuous ring-like member is made of an extrudable, biologically tolerable plastic.

6. An intraocular lens according to claim 1 wherein said continuous ring-like member is made of propylene.

7. An intraocular lens according to claim 1 wherein the continuous ring-like member has a cross-sectional diameter of from about 0.15 mm to 0.25 mm.

8. An intraocular lens according to claim 1 wherein said supporting bosses are integrally formed with said lens body as a one-piece construction.

9. An intraocular lens according to claim 1 wherein said lens include at least three supporting bosses spaced about said peripheral portion of said rear surface.

10. An intraocular lens according to claim 1 wherein said lens holding means comprises two curved elongated and resilient haptic members, said haptic members being connected to selected ones of the supporting bosses and extending outwardly from said lens body along an arc exterior to the periphery of the lens body.

11. An intracular lens for implantation in the posterior chamber of a human eye adjacent the posterior capsule, after extracapsular extraction; said intraocular lens comprising:
   (a) an optical lens body having front and rear surfaces;
   (b) means for holding said lens body in said posterior chamber;
   (c) a plurality of supporting bosses attached to and extending rearwardly from a peripheral portion of said rear surface of said lens body, said bosses each having a free end; and
   (d) a continuous ring-like member made of an extrudable and resilient, biologically tolerable, plastic, said ring-like member being attached to said supporting bosses at said free ends thereof and forming a resilient seal with the posterior capsule of the eye when said lens body is implanted in the posterior capsule, said continuous ring-like member being spaced from said rear surface by said supporting bosses so as to form an open zone between said rear surface and said ring-like member; said continuous ring-like member being swedged to the free ends of said supporting bosses.

12. An intraocular lens according to claim 11 wherein said lens holding means comprises a plurality of lens centering haptic members attached to selected ones of said supporting bosses, said haptic members extending peripherally outwardly from said lens body.

13. An intraocular lens according to claim 11 wherein said continuous ring-like member is made of propylene.

14. An intraocular lens according to claim 11 wherein the continuous ring-like member has a cross-sectional diameter of from about 0.15 mm to 0.25 mm.

15. An intraocular lens according to claim 11 wherein said supporting bosses are integrally formed with said lens body as a one-piece construction.

16. An intraocular lens according to claim 11 wherein said lens include at least three supporting bosses spaced about said peripheral portion of said rear surface.

17. An intraocular lens according to claim 11 wherein said lens body is substantially plano-convex, said supporting bosses extending directly rearwardly from a planar rear surface of said lens body.

18. An intraocular lens for implantation in the posterior chamber of a human eye adjacent the posterior capsule, after extracapsular extraction comprising:
   (a) a lens body having a peripheral portion and front and rear surfaces;
   (b) means for holding said lens body in said posterior chamber;
   (c) a plurality of at least three supporting bosses attached to and extending directly rearwardly from said peripheral portion of said rear surface of said lens body, said supporting bosses each having a free end defining a slot therein; and
   (d) a continuous posterior ring made from an extrudable and resilient biologically tolerable plastic, said continuous ring-like member being swedged in said slots at said free ends of said supporting bosses, thereby spacing said continuous ring-like member from said rear surface and forming an open zone between said rear surface and said ring-like member, said ring-like member having a cross-sectional diameter which is less than said peripheral zone of said lens body and forming a resilient seal with the posterior capsule of the eye when said lens body is implanted in the posterior capsule, said continuous ring-like member engaging the posterior capsule along the entire circumferance of said ring-like member to inhibit migration of Elschnig's pearls into the area of the posterior capsule defined by said circumference.

19. An intraocular lens construction comprising:
   (a) a lens body having a rear surface with a peripheral portion;
   (b) a plurality of supporting bosses mounted on and extending rearwardly from said peripheral portion of said rear surface; each of said bosses having a free end; and
   (c) a ring-like structure swedged to said plurality of bosses; said ring-like structure, in cooperation with said plurality of bosses forming a continuous ring-like arrangement oriented rearwardly of said lens body rear surface and having a diameter no greater than said lens body;
   (d) whereby said continuous ring-like arrangement may selectively form a resilient seal with a posterior capsule of the eye when said intraocular lens construction is operatively positoned therein.

20. An intraocular lens construction according to claim 19, wherein said supporting bosses are oriented to provide an open zone at the rear surface of said lens body to permit selective insertion of an instrument therethrough.

* * * * *